United States Patent
Stein et al.

[11] Patent Number: 5,677,314
[45] Date of Patent: Oct. 14, 1997

[54] BIS(METHYLIDENE)PHENYLENE DERIVATIVES

[75] Inventors: Inge Stein, Rodgau; Michael Schwarz, Grosse-Gerau; Ulrich Heywang, Darmstadt; Michael Kompter, Riedstadt, all of Germany

[73] Assignee: Merck Patent Gesellschaft Mit Beschrankter Haftung, Darmstadt, Germany

[21] Appl. No.: 563,796

[22] Filed: Nov. 28, 1995

[30] Foreign Application Priority Data

Nov. 29, 1994 [DE] Germany .................. 44 42 324.1

[51] Int. Cl.$^6$ .................. A61K 31/46; C07D 453/02
[52] U.S. Cl. .................. 514/305; 546/137
[58] Field of Search .................. 546/137; 514/305

[56] References Cited

U.S. PATENT DOCUMENTS

| | | | |
|---|---|---|---|
| 4,705,519 | 11/1987 | Hayes et al. | 623/16 |
| 5,399,563 | 3/1995 | Stein et al. | 514/305 |

FOREIGN PATENT DOCUMENTS

| | | |
|---|---|---|
| 0 576 974 | 6/1993 | European Pat. Off. . |
| 42 04 922 | 2/1992 | Germany . |
| 2 121 801 | 6/1983 | United Kingdom . |
| 2 185 019 | 12/1986 | United Kingdom . |

OTHER PUBLICATIONS

Cecil Textbook of Medicine, ed. Wyngaarden, J.B. et al, 1992, pp. 1029–1032 and 2297–2298 Oct. 1992.

*Primary Examiner*—C. Warren Ivy
*Assistant Examiner*—Garth M. Dahlen
*Attorney, Agent, or Firm*—Millen, White, Zelano, & Branigan, P.C.

[57] ABSTRACT

The invention relates to bis(methylidene)phenylene derivatives of the formula $$A^1\text{-Phe-}A^2 \qquad I$$

wherein Phe is an unsubstituted or substituted phenylene group, $A^1$ is a group selected from the formulae 1, 2 and 3 and $A^2$ is a group other than $A^1$ selected from the formulae 1, 2 and 3

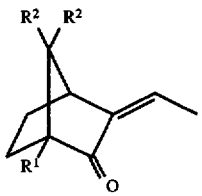

1

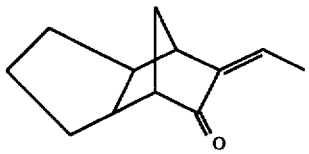

2

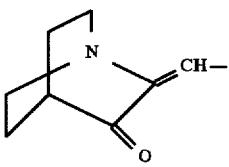

3 wherein $R^1$ and $R^2$ are independently H or $CH_3$ and their preparation and use as UV filters, in particular cosmetic and pharmaceutical preparations.

15 Claims, No Drawings

BIS(METHYLIDENE)PHENYLENE DERIVATIVES

FIELD OF THE INVENTION

The invention relates to bismethylidenephenylene derivatives of the formula I $$A^1\text{-Phe-}A^2 \qquad \qquad I$$

wherein

Phe is a phenylene group which is unsubstituted or substituted by 1 to 4 hydroxyl, alkyl or alkoxy groups having 1 to 10 C atoms, $A^1$ is a group selected from the formulae 1, 2, 3 and 4

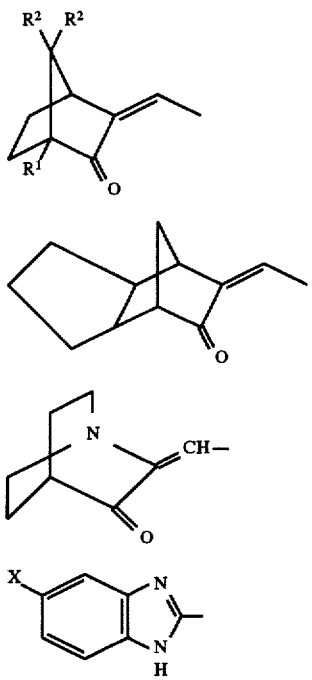

$R^1$ is H, $CH_3$ or $-CH_2SO_3H$, $R^2$ is H or $CH_3$, and X is H or $SO_3H$ and $A^2$ is a group other than $A^1$ selected from the formulae 1, 2, 3 and 4, and processes for their preparation and their use in cosmetic preparations, in particular for protection from solar radiation, and in pharmaceutical preparations for the prophylactic treatment of inflammations and allergies of the skin or certain types of cancer.

BACKGROUND OF THE INVENTION

As is known, the skin has a sensitive reaction to solar rays, which can produce ordinary sunburn or erythema, but also more or less pronounced burns.

Solar rays, however, also have other adverse effects: they cause the skin to lose its elasticity and to form wrinkles and thus lead to premature ageing. Dermatoses can sometimes also be observed. In the extreme case, skin cancer occurs in some people.

It is also desirable to protect hair against photochemical damage in order to prevent changes of color shades, bleaching or damage of mechanical type.

It is known that the components contained in cosmetic preparations are not always sufficiently photostable and decompose under the action of light rays.

As is known, the most dangerous part of the solar rays is formed by the ultraviolet rays having a wavelength of less than 400 nm. It is also known that owing to the presence of the ozone layer of the earth's atmosphere, which absorbs some of the solar radiation, the lower limit of the ultraviolet rays which reach the earth's surface is about 280 nm.

It thus appears desirable to make available compounds which can absorb UV rays in a wavelength range from 280 to 400 nm, i.e. also UV-B rays having a wavelength between 280 and 320 nm, which play a decisive part in the formation of photoerythema, and also UV-A rays having a wavelength between 320 and 400 nm, which bronze the skin but can also age it, favor the elicitation of an erythema reaction or increase this reaction in certain people or can even cause phototoxic or photoallergic reactions.

The sunscreen filters customary today in cosmetics are divided into UVA and UVB filters. While good filters are obtained in the UVB range (280–320 nm) using substances such as Eusolex® 6300 or Eusolex® 232, those used in the UVA range (320–400 nm) are affected by problems.

Dibenzoylmethanes such as Parsol® 1789 or Eusolex® 8020 are not of unlimited stability under UV irradiation, which on the one hand reduces the filter effectiveness with time and on the other hand can favor photosensitization of the skin in isolated cases. The benzophenones which are likewise used as UVA filters are of only limited solubility in the oils used in cosmetics, and they have a relatively low absorption. On the other hand, only a few water-soluble UVA filters are currently known, the UV absorption of which, however, is low.

Similar benzylidenecamphor derivatives are known, e.g. from EP 0 390 682; however, these do not have a tricyclodecanone or quinuclidinone group.

In WO 93/16978, similar compounds having only one ketotricyclo[5.2.1.0]decane group (2) are described.

In EP 0 576 974, similar compounds having only one quinuclidinone group (3) are described.

These, however, have relatively low solubility in organic solvents.

SUMMARY OF THE INVENTION

It has been found that bismethylidenephenylene derivatives of the formula I, wherein Phe is a phenylene group which is unsubstituted or substituted by 1 to 4 hydroxyl, alkyl or alkoxy groups, in particular an unsubstituted 1,4-phenylene group, have outstanding UVA filter properties. Their solubility in the oils used in cosmetics is very good, so that use concentrations, even in complicated formulations, of up to at least 10% of the preparation are possible.

The compounds according to the invention furthermore have an unusual photostability to UV radiation, which by far exceeds the stability of previously known UV filter substances; they are suitable, in particular, as UVA or UV wide-spectrum filters.

If the absorption in the UVB range has a minimum, this is not a disadvantage as a UVB filter can be additionally incorporated in the formulation without problems.

Furthermore, the compounds of the formula I can also be used for the prophylactic treatment of inflammations and allergies of the skin and for the prevention of certain types of cancer.

Apart from their good properties as filters, the compounds according to the invention are distinguished by a good thermal and photochemical stability.

These compounds furthermore have the advantage of being non-toxic or -irritant and completely harmless to the skin.

They disperse uniformly in the conventional cosmetic carriers and can in particular form a continuous film in fatty carriers; they can be applied to the skin in this way in order to form an effective protective film.

The invention thus relates to the compounds of the formula I given above, in particular wherein Phe is 1,4-phenylene which is unsubstituted or substituted by 1 or 2 alkoxy groups having 1 or 2 C atoms.

Phe is preferably a group of the formula

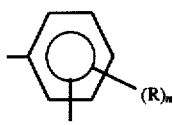

in particular a group of the formula

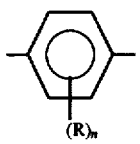

In this formula, R is a methyl, ethyl, n-propyl, i-propyl, n-butyl, i-butyl, t-butyl or 1,1,3,3-tetramethylbutyl radical, methoxy, ethoxy, or 2-ethylhexyloxy radical or hydrogen, preferably hydrogen.

n is 1 to 4, preferably 1 or 2.

The phenylene group is preferably unsubstituted or substituted by one or two alkoxy groups having 1 to 8 C atoms, in particular by methoxy, ethoxy or 2-ethylhexyloxy groups.

Preferred compounds of the formula I are those of the formulae I1 to I10, $A^1$ being a group of the formula 1, 2 or 3 and $A^2$ being a group of the formula 1, 2 or 3 and R being alkyl or alkoxy having 1 to 10 C atoms.

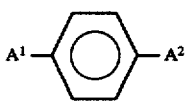

I1

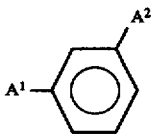

I2

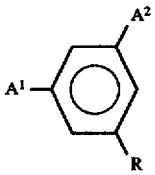

I3

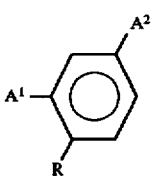

I4

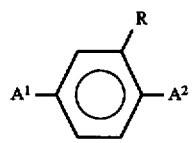

I5

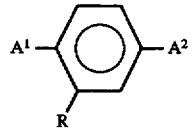

I6

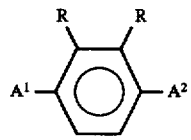

I7

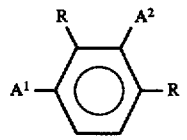

I8

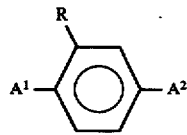

I9

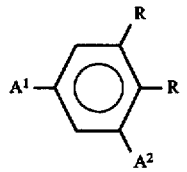

I10

Among these, the compounds of formulae I1, I2, I3 and I4 are particularly preferred.

Those compounds of the formula I and formulae I1 to I10 are additionally preferred wherein $A^1$ is camphor (formula 1, $R^1$ and $R^2$=CH$_3$) and $A^2$ is norcamphor (formula 1, $R^1$ and $R^2$=H).

The compounds of the formula I are obtained e.g. by reacting a benzaldehyde derivative of the formula II YHC-Phe-CHO      II wherein Phe has the meaning indicated, and Y is $A^1$ or O, with 8-ketotricyclo[5.2.1.0$^{2,6}$]decane, norcamphor or quinuclidinone in the presence of a base.

As a rule, the reaction is carried out in an inert diluent, preferably a protic solvent, in particular an alcohol, such as e.g. methanol, ethanol, isopropanol or tert-butanol or an aprotic solvent, such as diethyl ether, toluene or cyclohexane or mixtures of the solvents mentioned. The bases employed are preferably alkali metal alkoxides, such as e.g. sodium methoxide, sodium ethoxide or potassium tert-butoxide.

The reaction can be carried out at temperatures between 0° C. and the boiling point of the reaction mixture, preferably at 25° to 60° C.

The aldehydes of the formula II are known or are prepared according to known methods.

8-Ketotricyclo[5.2.1.0$^{2,6}$]decane, norcamphor and quinuclidinone are known and commercially available.

The compounds of the formula I are obtained, for example, by reacting a protected formylbenzaldehyde derivative of the formula III (R$^3$O)$_2$CH-Phe-CHO      III wherein R³ is alkyl having 1 to 10 C atoms, or (R³O)₂CH is a 1,3-dioxan-2-yl or a 1,3-dioxacyclopent-2-yl group, with 8-ketotricyclo[5.2.0²·⁶]decane or quinuclidinone in the presence of a base, and hydrolysing the resulting acetal of the formula IV (R³O)₂CH-Phe-A²        IV in a manner known per se.

The resulting methylidine benzaldehyde of the formula II

OCH-Phe-A²        II is reacted in the presence of a base with camphor, norcamphor, 8-ketotricyclo[5.2.1.0²·⁶]decane or quinuclidinone in a manner known per se.

The invention also relates to the process for the preparation of the novel compounds of the formula I.

The invention further relates to the novel intermediates of the formulae IV and V, wherein A² is a group of the formula 2 or 3.

The invention further relates to a cosmetic preparation, which contains an effective amount of at least one derivative of the above formula I in a cosmetically tolerable carrier.

The cosmetic composition according to the invention can be used as an agent for the protection of the human epidermis or of the hair or as a sunscreen composition.

The invention further relates to a process for the protection of the skin and natural or sensitized hair from solar rays, an effective amount of at least one compound of the formula I being applied to the skin or the hair.

"Sensitized hair" means hair which has been subjected to a permanent wave treatment or a coloring or bleaching process.

The invention further relates to a colored or uncolored light-stabilized cosmetic preparation which comprises an effective amount of at least one bis(methylidene)phenylene derivative of the above formula I.

If the cosmetic composition according to the invention is used as an agent for the protection of human epidermis against UV rays, it is present in various forms customarily used for this type. Thus, it can be present, in particular, in the form of oily or oily-alcoholic lotions, emulsions, such as a cream or as a milk, in the form of oily-alcoholic, oily-aqueous or aqueous-alcoholic gels or as solid sticks or be formulated as an aerosol.

It can contain cosmetic adjuvants which are customarily used in this type of composition, such as e.g. thickeners, softeners, moisturizing agents, surface-active agents, preservatives, agents against foam formation, perfumes, waxes, lanolin, propellants, colourants and/or pigments which color the composition itself or the skin, and other ingredients usually used in cosmetics.

As a rule, the compound of the formula I is contained in an amount from 0.5 to 10%, preferably 1 to 8%, in particular 1 to 5%, relative to the total weight of the cosmetic composition for the protection of human epidermis.

These solubilizing agents used can be an oil, wax or other fatty substance, a lower monoalcohol or a lower polyol or mixtures thereof. The particularly preferred monoalcohols or polyols include ethanol, i-propanol, propylene glycol, glycerol and sorbitol.

A preferred embodiment of the invention is an emulsion which is present as a protective cream or milk and apart from the compound of the formula I comprises fatty alcohols, fatty acid esters, in particular triglycerides of fatty acids, fatty acids, lanolin, natural or synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or on a glycol, such as propylene glycol, and/or on a polyol, such as glycerol, and oils, waxes and fatty acid esters, such as triglycerides of fatty acids.

The cosmetic composition according to the invention can also be present as an alcoholic gel which comprises one or more lower alcohols or polyols, such as ethanol, propylene glycol or glycerol, and a thickener, such as silica. The oily-alcoholic gels additionally contain natural or synthetic oil or wax.

The solid sticks consist of natural or synthetic waxes and oils, fatty alcohols, fatty acid esters, lanolin and other fatty substances.

The invention also relates to cosmetic sunscreen compositions which contain at least one compound of the formula I and can include other UVB and/or UVA filters.

In this case, as a rule the amount of the filter of the formula I is between 1.0 and 8.0% by weight, based on the total weight of the sunscreen composition.

If a composition is formulated as an aerosol, as a rule the customary propellants are used, such as alkanes, fluoroalkanes and chlorofluoroalkanes.

If the composition according to the invention is to protect natural or sensitized hair from UV rays, it can be present as a shampoo, lotion, gel or emulsion for rinsing out, the particular formulation being applied before or after shampooing, before or after colouring or bleaching, or before or after permanent waving; or the composition is present as a lotion or gel for hairdressing and treatment, as a lotion or gel for brushing or setting a water-wave, as a hair lacquer, permanent wave composition, or colouring or bleaching composition for the hair. Apart from the compound according to the invention, this composition can contain various adjuvants used in this type of composition, such as surface-active agents, thickeners, polymers, softeners, preservatives, foam stabilizers, electrolytes, organic solvents, silicone derivatives, oils, waxes, antigrease agents, colourants and/or pigments which colour the composition itself or the hair or other ingredients customarily used for hair care. As a rule, the composition contains 1.0 to 5.0% by weight of the compound of the formula I.

The present invention also relates to cosmetic compositions which contain at least one compound of the formula I as an agent for protection from UV rays and as an antioxidant; these compositions include hair products, such as hair lacquers, water-wave lotions for setting the hair, optionally for treatment or easier hairdressing, shampoos, colouring shampoos, hair coloring compositions, make-up products, such as nail varnish, creams and oils for skin treatment, make-up (foundation), lipsticks, skin care compositions, such as bath oils or creams and other cosmetic compositions which, with respect to their components, can raise problems with photostability and/or oxidation in the course of storage. As a rule, compositions of this type contain 1.0 to 5.0% by weight of a compound of the formula I.

The invention furthermore relates to a method for the protection of the cosmetic compositions from UV rays and oxidation, an effective amount of at least one compound of the formula I being added to these compositions.

The invention further relates to the use of the compounds of the formula I as sun filters having a large width of absorption in a wavelength range from 320 to 400 nm.

The invention further relates to the use of the compounds of the formula I as cosmetic products.

As already mentioned above, in the course of its investigations the applicant has additionally found that the compounds of the formula I have a significant pharmacological activity in the area of the preventive treatment of inflammations and skin allergies.

The invention also relates to the compounds of the formula I for use as medicaments.

The invention further relates to a pharmaceutical composition which contains an effective amount of at least one compound of the formula I as active compound in a non-toxic carrier or excipient.

The pharmaceutical composition according to the invention can be administered orally or topically.

For oral administration, the pharmaceutical composition is present in the form of pastilles, gelatine capsules, coated tablets or as a syrup, suspension, solution, emulsion, etc. For topical administration it is present as an ointment, cream, hair-cream, solution, lotion, gel, spray, suspension, etc.

This composition can contain inert or pharmacodynamically active additives, in particular hydrating agents, antibiotics, steroids or non-steroidal anti-inflammatory agents, carotenoids and agents against psoriasis.

This composition can also contain flavour-enhancing agents, preservatives, stabilizers, moisture regulators, pH regulators, osmotic pressure modifiers, emulsifiers, local anaesthetics, buffers, etc.

It can additionally be formulated in a manner known per se in delayed-release form or in a form in which the active compound is rapidly released.

Even without further details, it is assumed that a person skilled in the art can utilize the above description to the widest extent. The preferred embodiments are therefore only to be understood as a descriptive disclosure which is by no means limited in any way.

The complete disclosure of all applications, patents and publications mentioned hereinbefore and hereinafter and of corresponding German application P4442324.1 filed Nov. 29, 1994, is introduced into this application by way of reference.

The following examples are representative of the present invention.

EXAMPLE 1

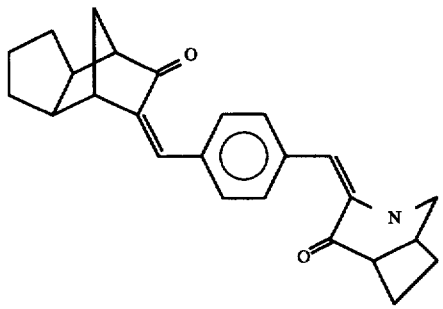

1A 9-(4-Formylbenzylidene)-8-ketotricyclo[5.2.1.0$^{2,6}$]decane

A suspension of 40 mmol (6.3 g) of 8-ketotricyclo [5.2.1.0$^{2,6}$]decane and 60 mmol of sodium methoxide (11 g of a 30% solution) in 50 ml of cyclohexane are stirred at 50° C. for 30 minutes. 50 mmol (9.0 g) of terephthalaldehyde monodimethyl acetal are then added dropwise and the mixture is refluxed for 1 hour. It is then cooled to room temperature and 100 ml of water are added.

The phases are separated and the aqueous phase is extracted with cyclohexane.

After evaporation under reduced pressure, the residue is taken up with acetone, treated with diluted hydrochloric acid and heated to boiling for 1 hour. After removal of the solvent by distillation, 1A is obtained, which is further processed in unpurified form.

1B 1-(8-Ketotricyclo[5.2.1.0$^{2,6}$]dec-9-ylidenemethyl)-4-(quinuclidinone-6-ylidenemethyl)benzene A suspension of 40 mmol (5.0 g) of quinuclidinone is reacted with 10 g of 1A in the presence of sodium methoxide analogously to Example 1A. After customary working up and recrystallization, 7.5 g=50.4% of the pure product are obtained.

Elemental analysis: Calculated: C: 80.12 H: 7.24 O: 8.61 N: 4.03 Found: C: 80.16 H: 7.26 O: 8.55 N: 4.03

UV (Ethanol, c=1 mg/100 ml): $\lambda_{max}$=349 nm

The following are prepared analogously:

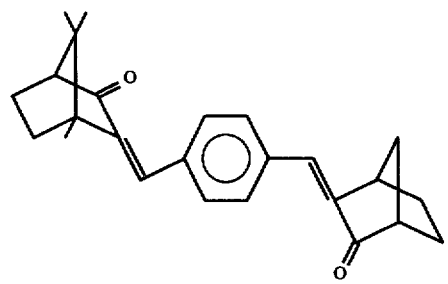

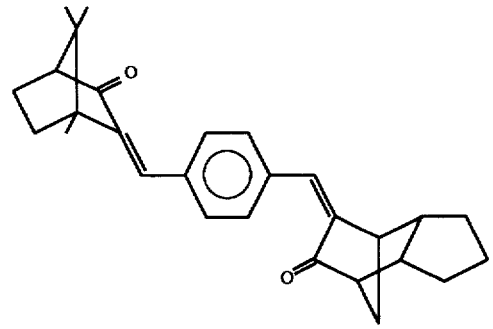

UV (Ethanol, c=1 mg/100 ml): $\lambda_{max}$=336 nm E=0.93

EXAMPLE 2

Sunscreen cream (W/O)

| | | | % |
|---|---|---|---|
| A | Compound from Example 1 | (1) | 3.00 |
| | Arlacel 581 | (2) | 7.00 |
| | Paraffin highly liquid (Item No. 7174) | (1) | 6.00 |
| | Arlamol S 7 | (2) | 2.00 |
| | Lunacera M | (3) | 5.00 |
| | Dow Corning 344 | (4) | 4.00 |
| | Miglyol 812 | (5) | 2.00 |
| | Oxynex 2004 (Item No. 6940) | (1) | 0.05 |

-continued

|   |                                              |     | %         |
|---|----------------------------------------------|-----|-----------|
| B | Glycerol (Item No. 4093)                     | (1) | 2.00      |
|   | Magnesium sulfate heptahydrate (Item No. 5882) | (1) | 0.17      |
|   | Preservative                                 |     | q.s.      |
|   | Water, demineralized                         |     | to 100.00 |

Preparation:

Heat phase A to 75° C. and phase B to 80° C. Slowly stir phase B into phase A. Homogenize. Cool with stirring. If desired perfume at 40° C.

Suppliers:
(1) E. Merck, Darmstadt
(2) ICI, Essen
(3) LW Fuller, Lüneburg
(4) Dow Corning, Düsseldorf
(5) Hüls Troisdorf AG, Witten

EXAMPLE 3

Sunscreen cream (O/W)

|   |                                 |     | %         |
|---|---------------------------------|-----|-----------|
| A | Compound from Example 1         | (1) | 3.00      |
|   | Emulsifier B 2155               | (2) | 8.00      |
|   | Stearic acid (Item No. 671)     | (1) | 2.00      |
|   | Paraffin liquid (Item No. 7162) | (1) | 6.00      |
|   | Paraffin non-caking (Item No. 7158) | (1) | 6.00  |
|   | Cetyl alcohol (Item No. 989)    | (1) | 2.50      |
|   | Miglyol 812                     | (3) | 9.50      |
|   | Abil AV 200                     | (2) | 0.50      |
|   | Cetyl palmitate (Item No. 15419)| (1) | 5.50      |
|   | Tocopherol acetate (Item No. 500952) | (1) | 0.05 |
| B | Glycerol (Item No. 4093)        | (1) | 3.00      |
|   | 1,2-Propanediol (Item No. 7478) | (1) | 2.00      |
|   | Karion F liquid (Item No. 2993) | (1) | 5.00      |
|   | Allantoin (Item No. 1015)       | (1) | 0.25      |
|   | Triethanolamine (Item No. 8377) | (1) | 0.50      |
|   | Preservative                    |     | q.s.      |
|   | Water, demineralized            |     | to 100.00 |

Preparation:

Heat phase A to 75° C. and phase B to 80° C. Slowly stir phase B into phase A. Homogenize. Cool with stirring. If desired perfume at 40° C.

Suppliers:
(1) E. Merck, Darmstadt
(2) Th. Goldschmidt, Essen
(3) Hüls Troisdorf AG, Witten

EXAMPLE 4

Sunscreen milk (W/O)

|   |                                 |     | %         |
|---|---------------------------------|-----|-----------|
| A | Compound from Example 1         | (1) | 3.00      |
|   | Pionier L-15                    | (2) | 19.00     |
|   | Paraffin viscous (Item No. 7160)| (1) | 15.00     |
| B | Glycerol (Item No. 4093)        | (1) | 5.00      |
|   | Magnesium sulfate heptahydrate (Item No. 5882) | (1) | 0.50 |
|   | Preservative                    |     | q.s.      |
|   | Water, demineralized            |     | to 100.00 |

Preparation:

Heat phase A to 75° C. and phase B to 80° C. Slowly stir phase B into phase A. Homogenize. Cool with stirring. If desired perfume at 40° C.

Suppliers:
(1) E. Merck, Darmstadt
(2) Hansen & Rosenthal, Hamburg

EXAMPLE 5

Sunscreen milk (O/W)

|   |                          |     | %         |
|---|--------------------------|-----|-----------|
| A | Compound from Example 1  | (1) | 3.00      |
|   | Eumulgin B 1             | (2) | 3.00      |
|   | Cutina MD                | (2) | 8.00      |
|   | Miglyol 812              | (3) | 7.00      |
| B | Glycerol (Item No. 4093) | (1) | 5.00      |
|   | Preservative             |     | q.s.      |
|   | Water, demineralized     |     | to 100.00 |

Preparation:

Heat phase A to 75° C. and phase B to 80° C. Slowly stir phase B into phase A. Homogenize. Cool with stirring. If desired perfume at 40° C.

Suppliers:
(1) E. Merck, Darmstadt
(2) Henkel, Düsseldorf
(3) Hüls Troisdorf AG, Witten

EXAMPLE 6

Sunscreen oil

|   |                                      |     | %     |
|---|--------------------------------------|-----|-------|
| A | Compound from Example 1              | (1) | 3.00  |
|   | Arlatone T                           | (2) | 2.00  |
|   | Miglyol 812                          | (3) | 16.00 |
|   | Cetiol B                             | (4) | 22.50 |
|   | Isopropyl myristate                  | (4) | 7.50  |
|   | Paraffin highly liquid (Item No. 7174) | (1) | 48.85 |
|   | Oxynex 2004 (Item No. 6940)          | (1) | 0.05  |
| B | Perfume oil                          | (5) | 0.10  |

Preparation:

Heat phase A to 70° C. with stirring until all components are dissolved, stir until cold and add phase B at 40° C.

Suppliers:
(1) E. Merck, Darmstadt
(2) ICI, Essen
(3) Hüls Troisdorf AG, Witten
(4) Henkel, Düsseldorf
(5) Haarmann & Reimer, Holzminden

We claim:

1. Bismethylidenephenylene derivatives of the formula I $$A^1\text{-Phe-}A^2 \qquad \qquad I$$

wherein

Phe is a phenylene group which is unsubstituted or substituted by 1 to 4 hydroxyl, alkyl or alkoxy groups having 1 to 10 C atoms, $A^1$ is a group selected from formula 3

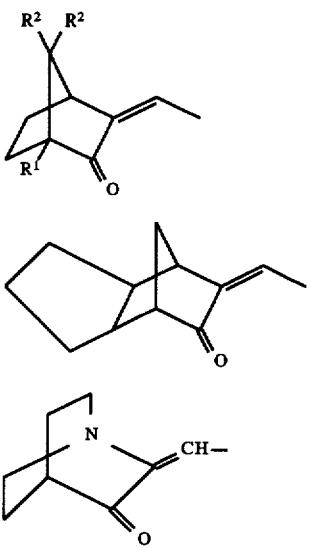

wherein
$R^1$ is H, $CH_3$ or —$CH_3$,
$R^2$ is H or $CH_3$, and
$A^2$ is a group other than $A^1$ selected from the formulae 1, 2 and 3.

2. Derivatives according to claim 1, wherein Phe is a phenylene group which is unsubstituted or substituted by 1 or 2 alkoxy groups having 1 to 10 C atoms.

3. Process for the preparation of compounds of the formula I according to claim 1 wherein $A^1$ and $A^2$ are each a group of the formula 2 or 3, characterized in that a formylbenzaldehyde derivative of the formula II YHC-Phe-CHO    II wherein Phe has the meaning indicated in claim 1, and Y is $A^1$ or O, is reacted with 8-ketotricyclo[5.2.1.0]decane or quinuclidinone in the presence of a base.

4. Process according to claim 3, characterized in that the base is an alkali metal alkoxide.

5. Cosmetic preparation, characterized in that it contains an effective amount of at least one compound of the formula I according to claim 1 in a cosmetically tolerable carrier.

6. Cosmetic preparation according to claim 5, characterized in that it contains 0.5 to 10% by weight of at least one compound of the formula I.

7. Cosmetic preparation according to claim 5, characterized in that it additionally contains a UV-B filter.

8. Compound of the formula I according to claim 1 within a medium suitable for use in a cosmetic product.

9. Compound of the formula I according to claim 1 within a medium suitable for use in a medicament.

10. Compound of the formula I within a medium suitable for use in the prophylactic treatment of inflammations and allergies of the skin.

11. Compound of the formula I within a medium suitable for use in the prevention of skin cancer of the type induced by ultraviolet radiation.

12. Pharmaceutical preparation, characterized in that it contains an effective amount of at least one compound of the formula I according to claim 1 in a physiologically acceptable carrier or excipient.

13. Pharmaceutical topical preparation according to claim 12.

14. A method of using a compound of the formula I according to claim 1 which comprises incorporating a compound of formula I in a medicament as an active ingredient for the treatment of inflammations, allergies and other ailments of the skin.

15. Bis(methylidene)phenylene derivatives of the formula I $A^1$-Phe-$A^2$    I wherein Phe is a phenylene group which is unsubstituted or substituted by 1 to 4 hydroxy, alkyl or alkoxy groups having 1 to 10 C atoms, $A^1$ is of the formula

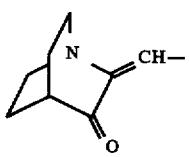

3

$A^2$ is a group selected from the formulae 1 and 2,

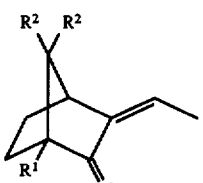

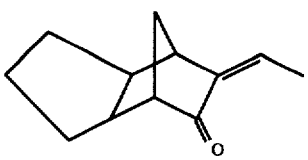

wherein
$R^1$ is H or $CH_3$, and
$R^2$ is H or $CH_3$.

* * * * *